United States Patent [19]

Green

[11] Patent Number: 5,339,701

[45] Date of Patent: Aug. 23, 1994

[54] NEEDLE INTERFACE APPARATUS

[75] Inventor: Thomas B. Green, Batavia, Ohio

[73] Assignee: Tekmar Company, Cincinnati, Ohio

[21] Appl. No.: 100,699

[22] Filed: Jul. 30, 1993

Related U.S. Application Data

[63] Continuation of Ser. No. 22,772, Feb. 23, 1993, abandoned, which is a continuation of Ser. No. 662,219, Feb. 28, 1991, abandoned.

[51] Int. Cl.$^5$ ............................................. G01N 30/18
[52] U.S. Cl. ................................. 73/864.86; 73/23.41
[58] Field of Search ........... 73/864.81, 864.86, 864.87, 73/864.74, 863.85, 23.41

[56] References Cited

U.S. PATENT DOCUMENTS

| | | | |
|---|---|---|---|
| 3,353,411 | 11/1967 | Nadeau et al. | 73/864.74 |
| 3,550,452 | 12/1970 | Halasz . | |
| 3,610,241 | 10/1971 | Le Marie | 73/864.86 |
| 3,693,455 | 9/1972 | Harding et al. | 73/864.86 |
| 4,000,654 | 1/1977 | Harris, Jr. . | |
| 4,274,285 | 6/1981 | Purgold | 73/863.31 |
| 4,402,911 | 9/1983 | Walters | 73/864.86 |
| 4,927,605 | 5/1990 | Dorn et al. | 73/864.86 |
| 5,081,872 | 1/1992 | Greter | 73/863.85 |

FOREIGN PATENT DOCUMENTS

| | | |
|---|---|---|
| 0437667A3 | 7/1991 | European Pat. Off. . |
| 0023959 | 7/1972 | Japan .................. 73/864.86 |
| 57-158551 | 9/1982 | Japan . |
| 60-115853 | 6/1985 | Japan . |

OTHER PUBLICATIONS

Supelco, division of Rohm & Haas, catalog 28, front and back covers, pp. 120 and 121 (1990).
Supelco Septum Nut Installation Instructions with diagrams (1988).

*Primary Examiner*—Thomas P. Noland
*Attorney, Agent, or Firm*—Westman, Champlin & Kelly

[57] ABSTRACT

A needle interface apparatus for maintaining a stable connection between a first instrument and a second instrument, such as an auto-sampler unit and a gas chromatograph. A needle interface apparatus is comprised of a modified septum nut on the second instrument which has a nipple, and a needle assembly having a sleeve positioned around the needle wherein the sleeve frictionally fits over the nipple of the modified septum nut. A support tube surrounds the needle assembly and connected transfer line from the first instrument to minimize flexing of the outlet tubing relative to the needle assembly.

12 Claims, 1 Drawing Sheet

NEEDLE INTERFACE APPARATUS

This is a continuation of application Ser. No. 08/022,772, filed Feb. 23, 1993 and now abandoned which was a continuation of application Ser. No. 07/662,219, filed Feb. 28, 1991 now abandoned.

FIELD OF THE INVENTION

The invention relates to an apparatus for maintaining a connection between the outlet of a first instrument for handling or analyzing gaseous sample and the inlet of a second instrument for handling or analyzing gases having a septum at the inlet thereof, such as a gas chromatograph. The invention limits movement of the needle inserted into the septum at the inlet of the second instrument.

BACKGROUND OF THE INVENTION

In various analytical procedures used to characterize a particular sample, it is often necessary to link the output of a first instrument to the input of a second instrument. For example, it is known to connect the output line of a gas chromatograph to the input of a mass spectrometer to permit analysis by the mass spectrometer of the components of a sample separated by the gas chromatograph. It is also known to directly link equipment which prepares a sample for analysis with the instrument which actually performs the analysis. For example, it is known to link the output line of an auto-sampler device to the input of a gas chromatograph to permit analysis by the gas chromatograph of the multiple samples prepared from vials cycled through the auto-sampler device.

In the case of the auto-sampler device as the first instrument and a gas chromatograph as the second instrument, the output of the auto-sampler device is typically linked to the input of the gas chromatograph by a needle brazed or otherwise connected to the output tubing of the auto-sampler. The needle is then inserted through a hole bored in the septum nut to pierce a septum at the input of the gas chromatograph, and sample is then transferred from the auto-sampler to the gas chromatograph.

Unfortunately, this arrangement suffers from several disadvantages. First, the needle is not fixed in position relative to the septum nut. As a result, the needle can be accidently pulled from the gas chromatograph, with loss of sample to the air. Second, because the needle is not supported at the septum, the downward force exerted by the weight of the needle tends to increase the size of the hole at the septum, allowing sample to leak back through the septum hole into the air. Third, in certain applications the output line from the auto-sampler is capillary tubing having very narrow diameters, in the range of 0.32 millimeter to 0.53 millimeter. This tubing is utilized where very small amounts of sample are available for analysis. Capillary tubing is very fragile and is susceptible to damage if not adequately supported.

SUMMARY OF THE INVENTION

The invention relates to an apparatus which aids in maintaining a connection between the output of a first instrument and the input of a second instrument, such as an auto-sampler and gas chromatograph, respectively. Specifically, the invention includes the combination of a modified septum nut for accepting a needle and a modified needle assembly for insertion into the septum nut. The needle assembly consists of a needle connected to a fitting with a sleeve positioned around the needle which covers at least a portion of the needle. The fitting on the needle assembly connects to the output tubing of the first instrument such as the auto-sampler device, to allow sample to flow through the fitting and out the tip of the needle. The modified septum nut attaches to the input of the second instrument, such as a gas chromatograph. The modified septum nut has a nipple with a longitudinal bore terminating at a cavity for accepting a septum. Preferably, the end of the bore opposite the cavity is countersunk to facilitate insertion of the needle. The outside diameter of the nipple is slightly smaller than the inside diameter of the sleeve to permit slidable mating and preferably frictional contact between the sleeve and the nipple as the needle is inserted into the longitudinal bore and through the septum. The invention further includes a support tube to protect the connection between the transfer line and the fitting of the needle assembly. The support tube has an inside diameter large enough to accept the end of the transfer line from the first instrument as well as the outside diameter of the sleeve. A releasable cable tie which fits into a slot on the support tube is used to secure the transfer line to the support tube, thereby restricting movement of the transfer line relative to the support tube. Finally, a thumbscrew inserted into a threaded radial bore in the support tube is employed to positively contact the outside diameter of the needle assembly sleeve to further limit movement of the support tube relative to the transferline.

It is therefore an object of the invention to provide an interface between the output of a first instrument and the input of a second instrument which maintains positive connection between these two instruments.

It is a further object of the invention to provide an interface apparatus for maintaining a fixed relation between a needle and the septum through which the needle is inserted.

It is yet a further object of the invention to provide an interface apparatus which limits movement of the transfer line from the first instrument relative to the needle assembly to be inserted into the septum of the second instrument.

These and other objects and advantages of the invention are described in more detail below, and are depicted in the drawings, in which:

DETAILED DESCRIPTION OF THE INVENTION

The invention in its broader aspects relates to a needle interface apparatus for maintaining a connection from an automatic sampler unit to an analyzing instrument comprising a needle connected to a fitting, a sleeve having a diameter greater than the needle which is fixed to the fitting and surrounds at least a portion of the needle, and a septum nut attachable to the analyzing instrument having a nipple with a longitudinal bore and a cavity behind the nipple for accepting a septum, wherein the needle is insertable through the bore to an extent sufficient to pierce the septum, and further wherein the inside diameter of the sleeve slidably mates with and preferably frictionally engages the outside diameter of the nipple as the needle is inserted into the bore. The needle is preferably welded to a fitting portion comprised of a hex head with a threaded tip which is countersunk, supplied as the Model SS-100-C fitting from Swagelok, Inc. To the hex head is welded a stainless steel sleeve, which surrounds the needle. The needle, preferably made from stainless steel such as grades 304 or 316, is inserted into the sleeve opposite the threaded tip and brazed to fix the needle in position. Preferably, the sleeve is concentrically arrayed around the axis of the needle.

The outlet tubing from the first instrument is connected to the needle by feeding the outlet tubing into a compression fitting nut, such as that supplied with the Model SS-100-C fitting manufactured by Swagelok, Inc. The outlet tubing is made from nickel alloy, stainless steel, or other material which does not evolve any substances which might affect analysis of the sample and which is not permeable to compounds in the air which might diffuse through the material and be carried to an analytical device.

The septum nut is a modification of that which is normally used on analyzing instruments such as gas chromatographs. The conventional septum nut attaches to the input of the gas chromatograph and has a cavity therein for accepting a septum and a bore on the outside face to accept a needle, which pierces the septum. The invention employs a modification of this septum nut, adding a nipple to the front face of the septum nut which is longitudinally bored to accept the needle. The outside diameter of the nipple is slightly smaller than the inside diameter of the sleeve to permit the nipple to slidably mate with the sleeve as the needle pierces the septum.

Figure 1:
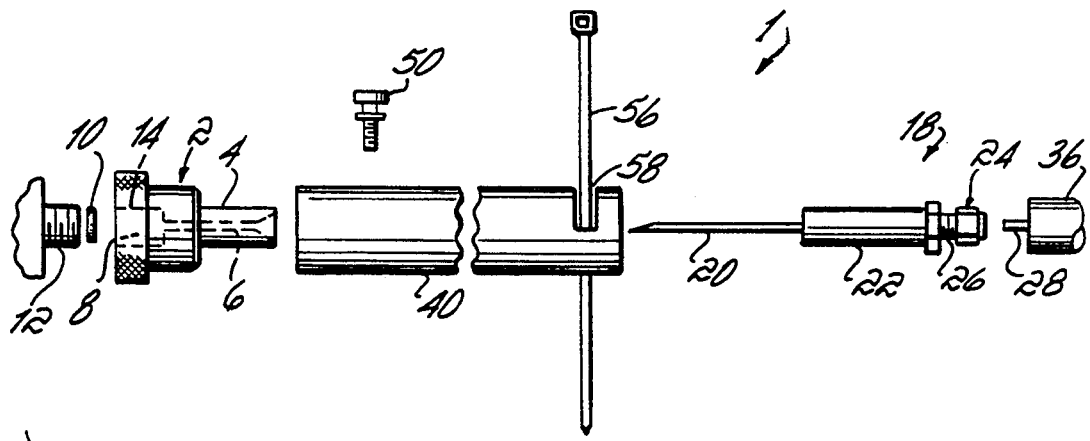
FIG. 1 is a disassembled view showing the components of the needle interface apparatus prior to assembly.

Referring to the drawings, FIG. 1 shows the components of the Interface Apparatus 1 prior to final assembly. Septum nut 2 has a nipple 4 through which is drilled a longitudinal bore 6. Behind the nipple 4 is cavity 8 into which is positioned septum 10. The inside walls 14 of septum nut 2 which define the cavity 8 are preferably threaded to connect to the inlet port 12 of an analyzing device. The end of the longitudinal bore 6 opposite cavity 8 is preferably countersunk to facilitate insertion of the needle. The inside diameter of cavity 8 varies, because different dimensions are necessary to accommodate the variety of sizes of inlet ports 12 produced by different manufacturers. Likewise, septa are produced in different sizes to accommodate the specific requirements of individual manufacturers. The septa are typically made from inert, deformable materials having a low tendency to leak after being pierced by a needle, such as poly(tetrafluoroethylene)-faced silicone or butyl rubber.

Figure 3:
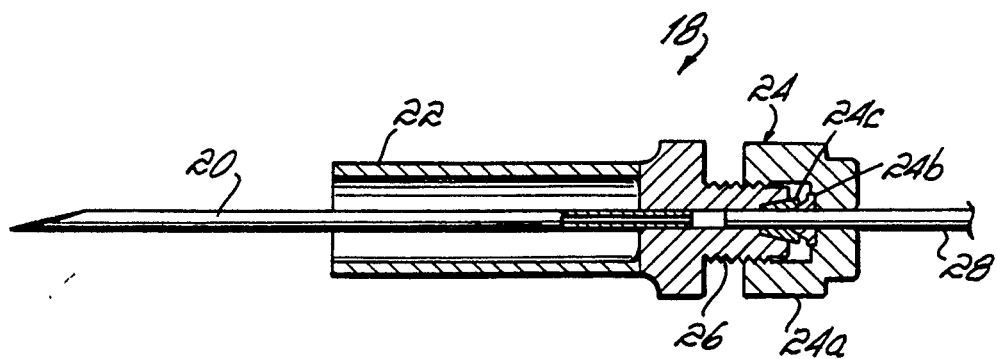
FIG. 3 is a cross sectional view in detail of the needle assembly component of the apparatus.

The needle assembly 18 consists of a needle 20 positioned within a sleeve 22, terminating at a fitting 24. Preferably, the sleeve 22 is welded onto the base portion of a compression fitting, such as the Swagelok Model SS-100-C, opposite the threaded extension which mates with a cap unit, described in more detail below. The needle 20 is preferably secured inside the sleeve 22 by fitting the needle 20 into the bore of the base portion of the compression fitting and then welding the base of the needle 20 to the base portion of the compression fitting around the bore thereof, prior to welding of the sleeve 22 as best shown in FIG. 3. Alternatively, however, other means of securing the needle 20 to the sleeve 22 can be employed, such as by use of a threaded connection, adhesives or the like.

As shown in FIG. 3, the fitting 24 is preferably a compression fitting which accepts an outlet tubing 28 from the first instrument through a center hole in the compression cap nut 24a and forms an airtight connection by the action of screwing the cap 24a nut onto the threaded extension 26. As cap nut 24a is tightened onto threaded extension 26, the back ferrule 24b and front ferrule 24c, which fit into the countersunk end of threaded extension 26, are forced to swage onto the inserted outlet tubing 28 to form the connection. Temperature fluctuation along the outlet tubing 28 is minimized by the use of insulation, independent heating means, or a combination of the two, which is enclosed within the tubing wrap 36.

Figure 2:
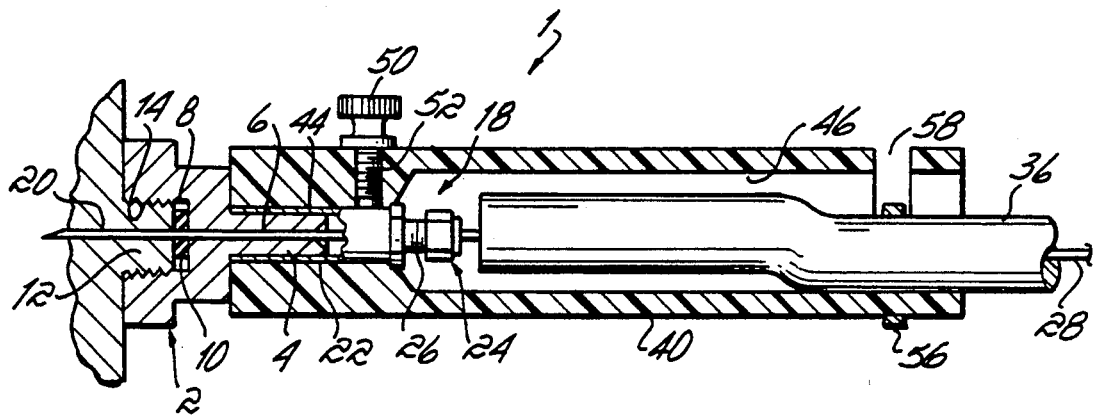
FIG. 2 is a cross sectional view of the needle interface apparatus after assembly.

As shown in FIGS. 1 and 2, a support tube 40 is used to limit flexing of the outlet tubing 28 relative to the needle assembly 18. This is particularly useful where the outlet tubing is of a very narrow diameter, such as in the case of capillary tubing where small amounts of sample are being processed. The interior diameter of support tube 40 is bored to permit the needle assembly 18 and outlet tubing 28 coated with tubing wrap 36 to fit inside. As shown in FIG. 2, the interior dimensions of the support tube 40 are bored to two different inside diameters, one being larger than the outside diameter of the needle assembly 18, and the second being slightly larger than the outside diameter of the tubing wrap 36. The interior volumes of the support tube 40 after boring are designated as needle assembly cavity 44 and tubing wrap cavity 46, respectively. This internal bore arrangement minimizes free movement of the support tube 40 around the needle assembly 18 and tubing wrap 36 after insertion. After the needle assembly 18 and outlet tubing 28 covered with tubing wrap 36 have been inserted into the support tube 40, the support tube 40 is secured onto the outside diameter of the sleeve 22 by tightening thumbscrew 50 onto the sleeve 22 through radial bore 52. The support tube 40 is secured to tubing wrap 36 by tightening releasable cable tie 56 which fits through slot 58.

FIG. 2 shows the interface apparatus in the assembled position, with the inside diameter of sleeve 22 frictionally contacting the outside diameter of nipple 4. Needle 20 is shown inserted into longitudinal bore 6 to pierce septum 10 located inside cavity 8. Typically, the needle assembly 18 connected to outlet tubing 28 covered by tubing wrap 36 is inserted into support tube 40 and the securing connections are made. This intermediate assembly then makes contact with septum nut 2 by inserting needle 20 into longitudinal bore 6 and pressing downward until sleeve 22 covers the entire nipple 4.

Because the analyzing instruments of various manufacturers have inlet ports of varying dimensions, septum nuts 2 are manufactured having a variety of inside wall 14 threaded diameters. The outside diameter of nipple 4, however, is a single diameter, typically 0.249/0.248 inch (6.325/6.299 millimeter) to accept a standard inside diameter of 0.255/0.251 inch (6.477/6.375 millimeter) of sleeve 22. Therefore, the inside diameters of needle assembly cavity 44 and tubing wrap cavity 46 are typically of a standard size, being 0.301/0.291 inch (7.645/7.391 millimeter) and 0.765/0.735 inch (19.431/18.669 millimeter) respectively.

The needle interface apparatus 1 provides a stable connection between the outlet 28 of the first instrument and the inlet 12 of the second instrument, and further protects the connection between the outlet tubing of the first instrument and the fitting of the interface apparatus from flexing, which creates an additional risk of loss of sample to the air. It can be seen, however, that even though a stable connection has been made, the needle 18 can be readily removed from the septum nut 2 of the analyzing instrument.

Thus it is apparent there has been provided, in accordance with the invention, a needle interface apparatus that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the present invention.

I claim:

1. A needle interface apparatus for maintaining a connection from an automatic sampler unit to an analyzing instrument comprising:
   a needle connected to a fitting;
   a sleeve having a diameter greater than said needle, said needle affixed to said fitting and a portion of said sleeve surrounding at least a portion of said needle; and
   a septum nut attachable to the analyzing instrument having a nipple at a first end with a longitudinal bore, and a cavity at a second end within said septum nut for accepting a septum sealingly held within said cavity when said septum nut is attached to a part of the analyzing instrument, and further wherein said sleeve slidably mates with said nipple as said needle is inserted into said bore.

2. The apparatus of claim 1 wherein said sleeve is concentrically arrayed around the axis of said needle.

3. The apparatus of claim 1 wherein said sleeve is longer than said nipple.

4. The apparatus of claim 1 wherein said fitting is a compression fitting.

5. The apparatus of claim 1 having a support tube with an inside diameter greater than the outside diameter of said sleeve and a transfer line connected to said fitting, said support tube surrounding at least a portion of said sleeve and said transfer line, and secured to said transfer line.

6. The apparatus of claim 5 where said support tube is secured to said transfer line by a releasable cable tie.

7. The apparatus of claim 6 wherein said support tube is radially bored and threaded to accept a thumbscrew.

8. In a septum nut attached to an analyzing instrument having a septum, the septum nut having a cavity for receiving the septum when the septum nut is attached to the analyzing instrument the improvement comprising a nipple with a longitudinal bore therethrough, said nipple formed on said nut opposite of said cavity whereby when a needle is inserted into said bore a sufficient distance said needle can contact and penetrate said septum, said nipple slidably mating with a sleeve connected to and surrounding at least a portion of said needle.

9. The septum nut of claim 8 further characterized in that said bore in said nipple is countersunk.

10. A needle interface apparatus for maintaining a connection from an automatic sampler unit to an analyzing instrument comprising:
    a needle connected to a fitting;
    a septum nut attachable to the analyzing instrument having a nipple with a longitudinal bore and a cavity behind said nipple for accepting a septum, wherein said needle is insertable through said bore to an extent sufficient to pierce said septum;
    a sleeve having a diameter greater than said needle, said sleeve affixed relative to said fitting and surrounding at least a portion of said needle; and
    wherein said sleeve slidably mates with said nipple as said needle is inserted into said bore.

11. The apparatus of claim 10 further characterized by said sleeve being concentrically arrayed around a central longitudinal axis of said needle.

12. The apparatus of claim 10 and a support tube with an inside diameter greater than the outside diameter of said sleeve, and a transfer line connected to said fitting, said support tube surrounding at least a portion of said sleeve and said transfer line, and being secured by said transfer line.

* * * * *